United States Patent [19]

Roberts et al.

[11] Patent Number: 4,535,486
[45] Date of Patent: Aug. 20, 1985

[54] LOW FRICTION BEARING SURFACES AND STRUCTURES PARTICULARLY FOR ARTIFICIAL PROSTHETIC JOINTS

[75] Inventors: Jack Roberts, Farmington Hills, Mich.; Robert L. Johnson, Edina, Minn.

[73] Assignee: Rensselaer Polytechnic Institute, Troy, N.Y.

[21] Appl. No.: 264,950

[22] Filed: May 18, 1981

[51] Int. Cl.³ .............................................. A61F 1/04
[52] U.S. Cl. ................................... 623/22; 128/92 C; 128/92 CA; 623/18
[58] Field of Search .................... 3/1, 1.9, 1.91, 1.911, 3/1.912; 128/92 C, 92 CA; 523/457, 458; 252/12, 12.2

[56] References Cited

U.S. PATENT DOCUMENTS

| | | | |
|---|---|---|---|
| 2,956,039 | 10/1960 | Novak et al. | 523/458 |
| 3,455,864 | 7/1969 | Dodson | 252/12.2 |
| 3,893,196 | 7/1975 | Hochman | 3/1.913 |
| 3,910,857 | 10/1975 | Phillips | 523/458 |
| 3,994,814 | 11/1976 | Cairns | 252/12 X |
| 4,018,944 | 4/1977 | Hallstrom et al. | 523/457 X |
| 4,155,896 | 5/1979 | Rennier et al. | 523/458 X |
| 4,195,368 | 4/1980 | Patrichi | 3/1.912 X |
| 4,222,128 | 9/1980 | Tomonaga et al. | 3/1.9 |
| 4,263,681 | 4/1981 | Notton | 3/1.912 X |
| 4,294,745 | 10/1981 | Schmid et al. | 523/457 X |
| 4,336,617 | 6/1982 | Shikita et al. | 3/1 X |

FOREIGN PATENT DOCUMENTS 2413078  8/1979  France .................................... 3/1.9

OTHER PUBLICATIONS

Roberts, et al., "Design of a Continuous Fiber Composite Surface Hip Replace", Oct. 1980, vol. 101, Journal of Mechanical Design.

Primary Examiner—Richard J. Apley
Assistant Examiner—David J. Isabella
Attorney, Agent, or Firm—McGlew and Tuttle

[57] ABSTRACT

A slide bearing surface element is disclosed which can be used in prosthetic joints or mechanical bearing devices. The element has a composite coating made of a matrix of epoxy resin with particles of $Al_2O_3$ dispersed therein. Cu or stainless steel particles are included to increase thermal conductivity.

3 Claims, 8 Drawing Figures

LOW FRICTION BEARING SURFACES AND STRUCTURES PARTICULARLY FOR ARTIFICIAL PROSTHETIC JOINTS

FIELD AND BACKGROUND OF THE INVENTION

The present invention relates in general to slide bearing surfaces and bearing elements and in particular, to a new and useful slide bearing surface element which can be used in mechanical bearings and particularly in prosthetic joint replacements.

It is known to replace joints in the body, for example a hip joint, with artificial or prosthetic joints. An example is to replace the head of the femur or large leg bone with a metal ball made of stainless steel or vitallium. The socket in the pelvis or acetabulum is enlarged and a cup is inserted and secured to the pelvis for receiving the metal ball. Such joints are long lasting, however, they do not reproduce the resiliency and thermal characteristics of the living hip joint and are therefore, not entirely acceptable.

Some examples of prior art approaches to joint replacements can be found in U.S. Pat. No. 4,123,806 to Amstutz et al. Here it is disclosed that the cup can be made of ultra high molecular weight polyethylene and that a thin metal shell can be used rather than a total metal ball replacement, over the femoral head. Other examples of the prior art can be found in U.S. Pat. No. 3,829,904 to Ling et al, U.S. Pat. No. 3,723,995 to Baumann, U.S. Pat. No. 3,924,275 to Heinke et al, U.S. Pat. No. 3,893,196 to Hochman and U.S. Pat. No. 4,195,368 to Patrichi.

As already mentioned, many of the currently available artificial hip joints are made of a metal femoral replacement stem articulating within an ultra high molecular weight polyethylene, UHMWPE, cup. Both elements are secured with acrylic bone cement. In addition to the lack of resiliency noted above, these hip replacements suffer from additional problems including bone resorption, acrylic bone cement failure, and a loss or fatigue of the metal stem. This has led to so called cup or shell arthroplasty. In this technique only a layer of bone is removed from the femoral head and from the interior of the acetabular cup. The removed bone is replaced by matching cups and shells, the shell fastened over the remaining femoral head and the cup fastened into the enlarged acetubulum. Since the shell is made of metal however, problems remain due to a mismatching of elasticity and other properties between the metal and the living bone which it replaces. Young's modulus of bone is from about $5 \times 10^4$ psi to about $3 \times 10^6$ psi. The Young's modulus for steel is about $30 \times 10^6$ psi. While replacing the metal shell with a plastic shell might advantageously change the elasticity to be closer to that of bone, it is known in the art that plastic bearing parts can only be used in light loading applications, for example, of about 200 psi. For use particularly as a hip joint replacement, the joint must, however, be capable of withstanding 500 to 1,000 psi and, to be servacable for a relatively large number of years.

These considerations are also applicable to bearing or sliding elements such as gears, vanes, pistons and the like in mechanical applications other than prosthetic devices.

SUMMARY OF THE INVENTION

The present invention comprises, in its most elemental form, a wear resistant coating which can be used for sliding bearings or journals which is made of a matrix of cured epoxy having particles of $Al_2O_3$ dispersed therein. An additional component comprising particles of Cu or stainless steel is added to the matrix to increase the thermal conductivity of the coating which also contributes to its wear resistance.

According to the invention a slide bearing surface element can be made of a cured epoxy matrix with or without reinforcing glass fibers which has the aforementioned resilient coating thereon. The underlying matrix of reinforced or unreinforced epoxy resin provides resiliency to the overall element which has particular applications in prosthetic joint replacements and general applications to any mechanical device which utilizes elements which are in sliding contact with each other. The glass fibers can be oriented in any selected manner to increase the strength of the element as required. In the case of a replacement hip joint, the glass fibers can be oriented to roughly correspond to the trabecular structure of the bone in the area of the femoral head. The oriented fibers thus give strength to the femoral head replacement in the orientation at which it will receive most of its load while retaining resiliency of the femoral head replacement.

As already mentioned, a plastic shell replacement for a femoral head was previously considered as impractical. This was due in part to the low load usefulness of such plastic shells and also to the tendency of such plastic shells to loosen from the femoral head.

The present invention utilizes an epoxy resin reinforced by glass fibers for the femoral shell which has a composite coating of epoxy plus hard wear resistant particles having high thermal conductivity. The coating is used to "case harden" the surface of the otherwise unsuitable epoxy resin shell. The coated shell can be used in a UHMWP cup to produce a prosthetic joint replacement that can withstand the 500 to 1,000 psi load requirement.

The substantially all plastic design thus more closely mimics the elasticity of living bone and it therefore more acceptable. The use of the particles in the epoxy resin coating increases the otherwise poor thermal conductivity of the plastic joint to reduce wear which would be increased by higher temperatures at the interface.

Tests have been run using a coated ring shaped element according to the invention sliding against a fixed block. These tests reveal the wear resistance and suitability of the invention both for prosthetic joint replacements and for more generalized uses such as in gears, vanes, pistons, pumps, sleeves, journals and bearings.

An embodiment of the invention comprising a hip joint replacement was also tested and showed the same advantageous results.

The invention provides a wear resistant and thermally conductive coating for sliding elements which is simple in design, rugged in construction and economical to manufacture.

A method of making an element with such a coating is also disclosed.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
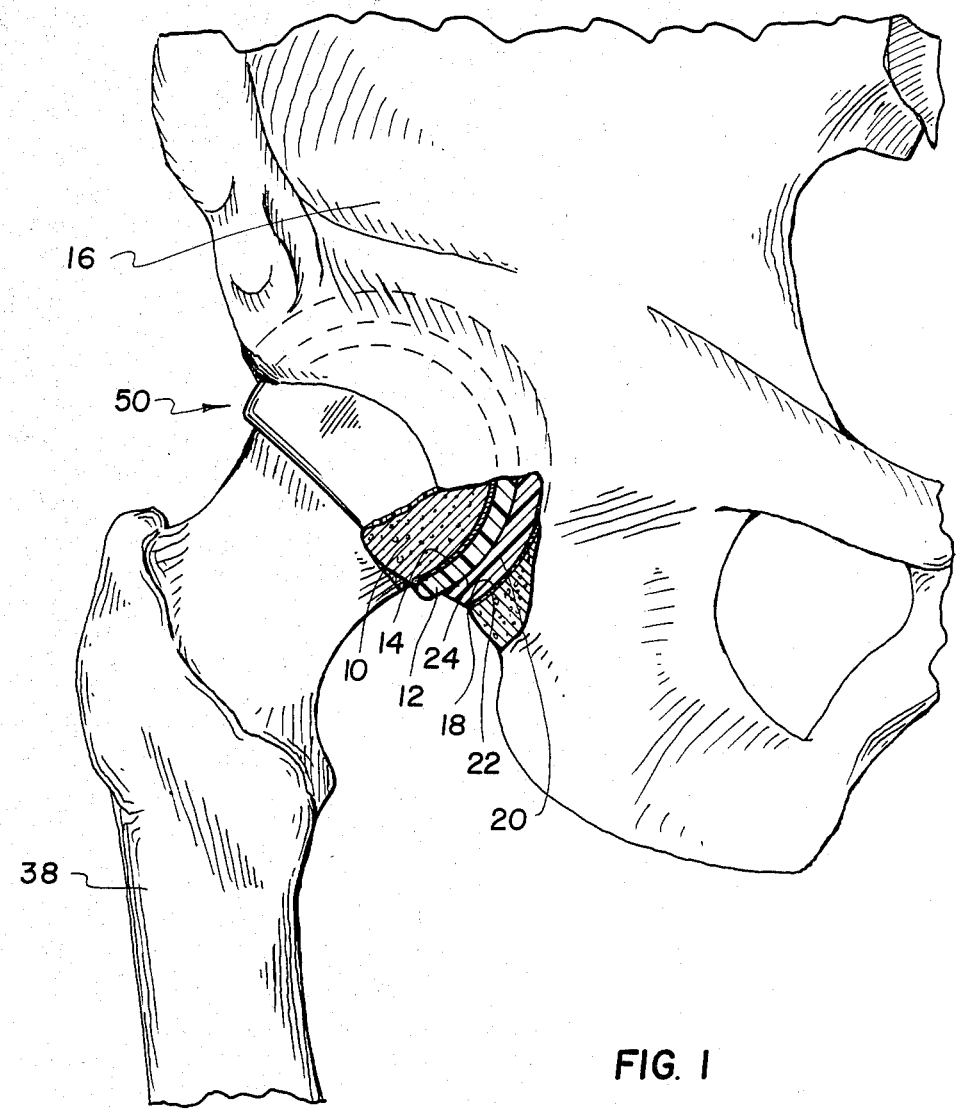
FIG. 1 is an elevational view partly in section of a hip joint with hip joint replacement according to the invention.

Turning to the drawings in particular, the invention embodied therein, in FIG. 1 comprises a hip joint replacement generally designated 50. According to the invention, the femoral head 10 is treated by removing a layer of bone therefrom. The layer of bone is replaced by an epoxy resin shell 12 which is glued to the remainder of the femoral head by acrylic bone cement 14.

Figure 3:
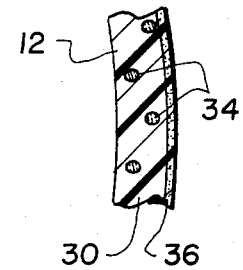
FIG. 3 is an enlarged partial sectional view of the femoral shell.

The socket 18 of the pelvis 16, the acetabulum, is also treated by removing a layer of bone therefrom. That bone is replaced by a cup 20 made, for example, of ultra high molecular weight polyethylene (UHMWPE). Cup 20 is cemented to the socket 18 using acrylic bone cement 22. To prevent excessive wear and heat buildup in an interface 24 between the sliding shell 12 and the cup 20, the invention provides the shell 12 with a composite coating. Details of the composite coating are shown in FIG. 3. The shell 12 comprises a matrix of epoxy resin 30 which can be reinforced according to one embodiment of the invention by E-glass fibers 34. A coating 36 is provided on the matrix 30 which is made up of the same or different epoxy resin as the matrix 30 which includes a selected proportion of hard particles, in particular $Al_2O_3$. The coating 36 may also include, in addition either particles of Cu or particles of stainless steel which have been found to increase the thermal conductivity of the coating 36 in an advantageous manner.

Figure 2:
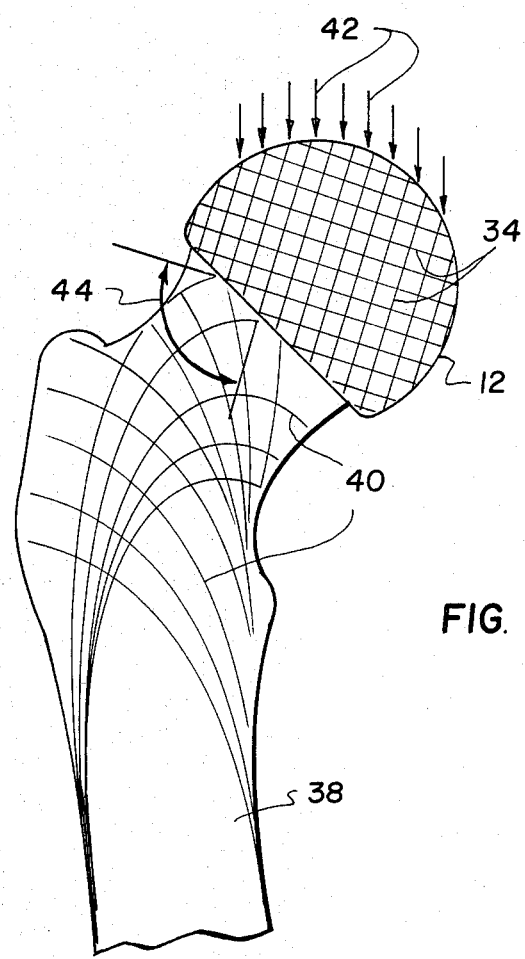
FIG. 2 is an elevational view of the top part of a femur or thigh bone showing the inventive shell over the femoral head thereof.

As shown in FIG. 2, a femur or thigh bone 38 has a particular internal structural orientation at its head region illustrated by lines 40. These lines illustrate the trabecular structure of the bone. Knowing the structure, the glass fibers 34 can be oriented to approximately mimic the extent of these lines to better reinforce the joint against the load illustrated by lines 42, the joint is most likely and most often exposed to. The fibers 34 can be oriented for example, at an angle 44 to each other, which can be for example 90°. Such orientation retains the resiliency of the plastic shell 12 while increasing its structural integrity in the direction most necessary.

Figure 4:
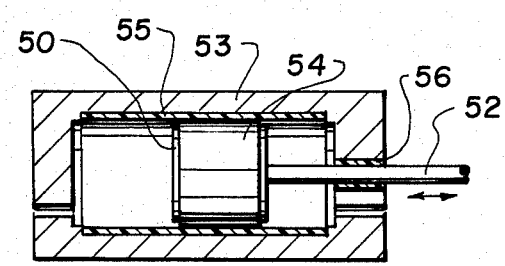
FIG. 4 is a simplified view of the invention utilized in a piston and cylinder arrangement.

FIG. 4 shows a more generalized version of the invention wherein a piston 50 having a piston rod 52 is movably mounted within a cylinder casing 53. According to the embodiment of FIG. 4, either the piston at 54 or the cylinder casing at 55 may be coated with the inventive coating or a slide element having the inventive coating. Reinforcing glass fibers may be utilized or deleted as necessary to withstand loads applied to the piston rod 52. The other of the coatings 54 and 55 may, for example, be UHMWPE material. In a similar fashion, the piston rod 52 itself and a bushing 56 may be equipped according to the invention to reduce wear between these two sliding elements.

Figure 5:
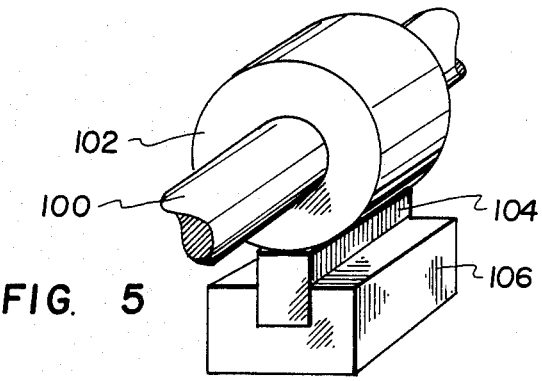
FIG. 5 is a simplified perspective view of a rotating ring and fixed block arrangement according to the invention.

Another simplified embodiment invention which is utilized primarily to illustrate the advantageous results achieved, is shown in FIG. 5 where a ring shaped member was carried on a rotatable shaft and caused to slide against a fixed block.

Friction tests were run on a standard LFW-1 wear test machine. A part of the machine is shown in FIG. 5. A shaft 100 carries a ring of epoxy 102 which is coated according to the invention. Ring 102 bears against a block of polyethylene 104 which is held in a holder 106. The apparatus used to load the stationary block against the rotating ring has been described in detail in an article by J. R. Jones, entitled "Low-Load Oscillating Tests of Bonded Solid Lubricants and Composites".** It consists briefly, of a loading system, the stationary specimen holder 106, the rotating test shaft 100, hydraulic friction pick-up and indicating dial gage. The secondary test block 104 was loaded against the rotating ring 102 with a 4.45N weight resulting, through a 30:1 lever magnification system, in an interfacial load of 134N. The shaft 100 to which the ring 102 was attached had a speed of 30 rpm corresponding to a linear surface velocity of $5.5 \times 10^{-2}$ ms$^{-1}$.

**(Lub. Engin., October, 1968, vol. 24, No. 10, 465–470.)

The epoxy used in this study consisted of a thermoset resin, Araladite 6010, and an aromatic diamine hardener, XU205, both.* The epoxy was formed by mixing 100 parts to 32 parts by weight of resin to hardener, respectively. The uncured epoxy was poured into silicone rubber molds for forming the rings (34.9 mm diameter and 9.5 mm wide) and placed in a pressure chamber located in an oven. A nitrogen tank was used to supply a constant pressure of 1.02 Pa during the curing process. The epoxy was gelled for two hours at 80° C., then postcured for four hours at 150° C. The particulate composite coating for the rings were prepared by machining the periphery of the rings by 0.3 mm in reduced diameter and then coating the surface of each ring with composite. The composite coatings consisting of hard particles (18-8 stainless steel, $Al_2O_3$, and the like) in uncured epoxy. The uncured epoxy plus particle mix was placed in and around the cured machined epoxy rings set in the ring molds. The final samples were then cured in the same manner as the epoxy rings without the coatings. The test specimens were polished to a final finish of 20–30μ inches CLA with 1 μm alpha-alumina.
(Trademarks of Ciba-Geigy, Inc., Ardsley, N.Y.)

Polyethylene blocks 104 used in the test were prepared from compression molded cylindrical blocks of 1900 U.H.M.W. polymer.* The blocks were machined into rectangular test blocks 15.8 mm long, 10.2 mm high and 6.4 mm wide and polished to a final finish of 60–80μ inches CLA with 600 grit silicon carbide paper. Both the test rings 102 and blocks 104 were cleaned in a methanolbenzene (10:1) mixture and oven dried at approximately 66° for 20 minutes prior to testing.
(Trademark of Hercules, Inc., Wilmington, Del.)

At the end of three hour screening tests using various ring compositions the most promising materials were selected to run in a 48-hour wear test. Both dry and wet tests using distilled water as the lubricant were run. In these tests the friction force, block center temperature and block wear scar width were recorded.

Studies of the ring and block wear surfaces were made using both an optical microscope and a scanning electron microscope.

For convenience the different type of materials used have been encoded as follows: material "A" defines a ring material made of 316 stainless steel. The material designated "B" comprises pure epoxy resin material used for the ring; the material designated "C" comprises an epoxy ring coated with a composite consisting of aluminum oxide having a particle size of 1 micron with epoxy in a 1:2 by weight ratio. Throughout the specification the ratios appearing in brackets will designate parts by weight for convenience. The material labeled "D" defines a ring of epoxy having a coating of (1:2) $Al_2O_3$/epoxy plus (3:20) Cu/epoxy with 16 microns particle size for the Cu.

The material designated "E" comprises an epoxy ring with composite coating of (1:2) $Al_2O_3$/epoxy plus (3:10) Cu/epoxy. The material designated "F" is a ring of epoxy with a composite coating of (1:2) $Al_2O_3$/epoxy plus (7:10) Cu/epoxy. The material "G" is epoxy ring with a composite coating of (2:1) 18-8 stainless steel-epoxy plus (3:10) $Al_2O_3$/epoxy with the stainless steel being in 64 micron particles. The codes for the different materials of the blocks is as follows: "I" is ultra high molecular weight polyethylene. "J" is (20:1) UHMWPE plus chopped graphite fibers supplied by Hercules Inc. of Wilmington, Del. The block designated "K" is (10:3) UHMWPE plus chopped graphite fibers.

Table 1 lists the coefficients of friction, block center temperature and block wear scar width for ring materials A through G when run dry against block materials I through K in the three-hour screening test. The coefficient of friction, block center temperature and wear scar width when the 316 stainless steel ring, material A, was run dry against an ultrahigh molecular weight polyethylene (UHMWPE) block, material I, were, respectively, 0.25, 29° C. and 3.5 mm. When a plain epoxy ring, material B, was run dry against UHMWPE, material I, the coefficient of friction, block center temperature and block wear scar width were, respectively, 0.20, 35° C. and 3.3 mm. These tests are shown for comparison. Addition of (1:2) parts by weight of $Al_2O_3$ to the epoxy according to the invention and resulting in material C, and running against block material I produced a 50% reduction in the coefficient of friction and a 5% reduction in the block center temperature. A further addition of from (3:20) to (7:10) parts by weight of copper (Cu) to the $Al_2O_3$/epoxy, (materials D, E or F) running against block I produced average values of the coefficient of friction, block center temperature and wear scar width of, respectively, 0.087±0.012, 29.7±2.1° C. and 3.30±0.00 mm. These values were 13%, 10%, and 6%, respectively, lower when compared to the same testing using the $Al_2O_3$/epoxy ring. When adding (2:1) parts by weight of the 18-8 stainless steel to the $Al_2O_3$/epoxy and running dry against block material I the coefficient of friction, block center temperature and block wear scar width were about the same as when the $Al_2O_3$/epoxy, material C, was used.

When (1:30) parts by weight of chopped graphite fibers were added to the UHMWPE block, resulting in material J, and when this material was run dry against ring material C the coefficient of friction, block center temperature and wear scar width were, respectively, 0.8, 28° C. and 4.1 mm. The coefficient of friction and block center temperature were, respectively, 20% and 15% lower than when a plain UHMWPE, material I, was used. Addition of (3:10) parts by weight of chopped graphite fibers increased the coefficient of friction by about 50% and the wear scar width by about 20% when run dry against ring material C. The plain UHMWPE is therefore preferred.

Ring material A, C, E and G were selected to run in the 48-hour wear test against block material I, the UHMWPE block, both dry and in the presence of distilled water or a lubricant. The coefficient of friction, block center temperature and block wear scar width are shown in Table 2. There was no substantial weight change in either the ring or block material, which would show excessive wear. The coefficient of friction, block center temperature and block wear scar width for the 316 stainless steel ring run dry against an UHMWPE block, material I, were respectively, 0.33, 31° C. and 3.6 mm. When the $Al_2O_3$/epoxy ring, material C was run dry against material I, the coefficient of friction remained about the same, while the block center temperature and wear scar width increased, respectively, 11% and 27%. Addition of (3:10) parts by weight of Cu to the $Al_2O_3$, epoxy, ring material E, resulted in reductions in the coefficient of friction, block center temperature and block wear scar width of, respectively, 15%, 9% and 4%. When the 18-3 stainless steel/epoxy ring was used the coefficient of friction, block center temperature and wear scar width were, respectively, 0.25, 32° C. and 3.6 mm. This resulted in a reduction of about 20% in the friction force when compared to the same test using ring material C, the $Al_2O_3$+Cu/epoxy ring, and a reduction in the friction force of about 24% when compared to using ring material A, the 316 stainless steel ring.

There was a reduction of 60-90% in the friction force, 10-24% in the block center temperature and 8-24% in the block wear scar width when running rings A, C E and G against block material I for 48 hours in distilled water as compared to running dry. When the surface condition was changed from no lubricant to distilled water the coefficient of friction, block center temperature and wear scar width for the $Al_2O_3$/epoxy ring, material C, decreased more than materials E, or G. The coefficient of friction, block center temperature and wear scar width when ring A was run in distilled water against block I were, respectively 0.07, 28° C. and 3.3 mm. Ring material C had the lowest coeifficient of friction (0.03) when run in distilled water against block material I. Materials C, E and G had coefficients of friction, block center temperatures and wear scar widths comparable to that when 316 stainless steel was run against UHMWPE in distilled water.

TABLE 1
RESULTS OF THREE-HOUR SCREENING TESTS, ALL SAMPLES RUN DRY

| Material | | Coefficient of Friction | Block Center Temperature °C. | Block Wear Scar Width mm |
| --- | --- | --- | --- | --- |
| Ring Code | Block Code | | | |
| A | I | .25 | 29 | 3.5 |
| B | I | .20 | 35 | 3.3 |
| C | I | .10 | 33 | 3.5 |
| C | J | .08 | 28 | 4.1 |
| C | K | .17 | 34 | 4.6 |
| D | I | .10 | 32 | 3.3 |
| E | I | .08 | 28 | 3.3 |
| F | I | .08 | 29 | 3.3 |
| G | I | .08 | 29 | 3.5 |

TABLE 2
RESULTS OF 48-HOUR WEAR TEST

| Material | | Lubricant | Coefficient of Friction | Block Center Temperature °C. | Block Wear Scar Width mm |
| --- | --- | --- | --- | --- | --- |
| Ring | Block | | | | |
| A | I | Dry | .33 | 31 | 3.6 |
| A | I | Distilled water | .07 | 28 | 3.3 |
| C | I | Dry | .30 | 35 | 4.9 |
| C | I | Distilled water | .03 | 27 | 3.7 |
| E | I | Dry | .25 | 32 | 4.7 |
| E | I | Distilled water | .10 | 28 | 3.7 |
| G | I | Dry | .25 | 32 | 3.6 |
| G | I | Distilled water | .07 | 28 | 3.3 |

In determining the relative thermal conductivities of the composite coatings a technique similar to that of Hyde, Cromwell and Arnold was employed (See their article "Piston Ring Coatings for High Performance Diesel Engines", SAE Transactions 76 (1968) 3107–3139). Low carbon steel rod stock was machined into 1.9 cm diameter buttons 1.27 cm long. Composite coatings according to the invention were applied to one flat surface of the buttons and ground to a uniform thickness of 0.50 mm. Two thermocouples were inserted in the button, equidistant from the center, 1.04 mm and 4.50 mm from the coated surface. A third thermocouple was attached to the uncoated surface and a fourth thermocouple to a hot plate. Heat was applied to the coated composite surface from the hot plate which was maintained at approximately 130° C. The buttons were placed in an asbestos block to prevent radiation losses from the cylindrical surface and the temperature readings were taken simultaneously over a three-minute period.

With this technique three temperatures at any given time were recorded for the steel button and the interface temperature between the composite coating and the hot plate. The temperatures in the steel button were then plotted versus distance from the composite surface and the interfacial temperature between the composite coating and the steel button was determined. This gave two known temperatures in the composite layer thus allowing a determination of the temperature gradient. Likewise, the temperature gradient in the steel button was determined, and from these temperature gradients and the thermal conductivity of the steel buttons, the thermal conductivity of the composite layer was determined as follows:

$$\text{Heat conduction in the steel button} = K_s(\Delta T/\Delta x)_s \quad (1)$$
$$\text{Heat conduction in the composite layer} = (K_c(\Delta T/\Delta x)_c \quad (2)$$

and in the absence of radiation losses the heat conducted in the steel is equal to the heat conducted in the composite layer, therefore:

$$K_s(\Delta T/\Delta x)_s = K_c(\Delta T/\Delta x)_c \quad (3)$$

Figure 6:
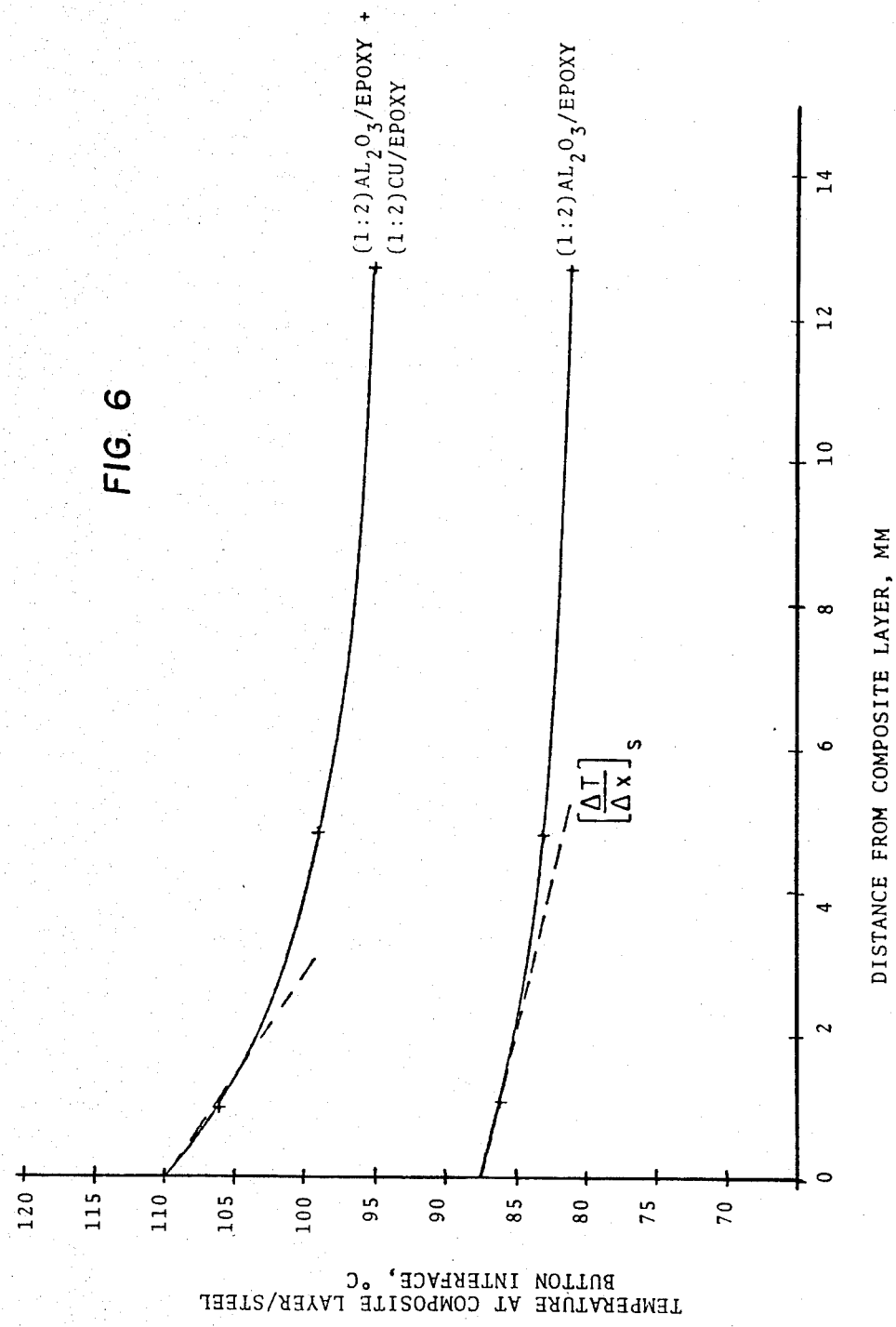
FIG. 6 is a graph relating the temperature of a portion of the composite coating against distance from the composite coating illustrating the heat conductivity of the inventive coating.

Therefore, the thermal conductivity of the composite layer was determined as:

$$K_c = K_s \left[ \frac{(\Delta T/\Delta x)_s}{(\Delta T/\Delta x)_c} \right] \quad (4)$$

where in Eqs. (1)–(4), $K_s$ is the thermal conductivity of steel, $K_c$ is the thermal conductivity of the composite layer, $(\Delta T/\Delta x)_s$ is the temperature gradient in steel and $(\Delta T/\Delta x)_c$ is the temperature gradient in the composite layer. FIG. 6 shows the plot of temperature at the composite layer/steel button interface versus distance from the composite layer for the (1:2) Al$_2$O$_3$/epoxy and the (1:2) Al$_2$O$_x$/epoxy+(1:2) cu/epoxy composite layers.

It appears that the addition of Cu, which increased the thermal conductivity of the composite from 0.18 kcal/hr·m·° C. for material C, the Al$_2$O$_3$/epoxy ring, to 1.70 kcal/hr·m·° C. for material E, the Al$_2$O$_3$+Cu/epoxy ring, helped increase wear resistance by transferring heat away from the contact area. The poor sliding properties of the copper in this small amount did not seem to affect the results. However, addition of the 18-8 stainless steel to the Al$_2$O$_3$/epoxy matrix and running dry for three of 48 hours against UHMWPE produced the same reduction in the coefficient of friction, block center temperature and wear scar width as when Cu was added to the Al$_2$O$_3$/epoxy. Since the thermal conductivity of (2:1) 18-8 stainless steel/epoxy+(3:10) Al$_2$O$_3$/epoxy was 0.42 kcal/hr·m·° C. and the thermal conductivity of the Al$_2$O$_3$+Cu/epoxy was 1.7 kcal/hr·m·° C., there appears to be a point above which an increase in the thermal conductivity no longer aids in reducing wear.

Among the epoxy coatings, the coefficient of friction was lowest for the Al$_2$O$_3$/epoxy and the wear scar width lowest for the 18-8 stainless steel+Al$_2$O$_3$/epoxy when run against UHMWPE in distilled water. Apparently, the distilled water helps conduct heat away from the contact area and inhibit the UHMWPE transfer layer. This, then results in lower friction forces and a smoother surface on the UHMWPE. Therefore, all of the composite coatings, materials C, E and G, run in distilled water during the 48-hour test had tribological properties very similar to that when 316 stainless steel was used as ring material.

The type of surface failure observed on the UHMWPE blocks when using ring materials C, E and G as the counterface materials was either adhesion, abrasion light scarring or fatigue. These same types of wear mechanisms can be seen when either 316 L stainless steel or surgical grade stainless is run against UHMWPE. The type of wear occurring apparently depends on many things, not the least of which are: environmental conditions, type of loading, the counterface roughness and the manner in which the two surfaces move against one another.

These studies have identified particular composites that can be substitutes for stainless steel or vitallium used in the total hip prosthesis.

The composite coatings consisting of (1:2) Al$_2$O$_3$/epoxy+(3:10) Cu/epoxy and (2:1) 18-8 stainless steel/epoxy+(3:10) Al$_2$O$_3$/epoxy, exhibited thermal, frictional and surface wear characteristics which were comparable to 316 stainless steel when all of these materials were run dry against UHMWPE. Composite coatings consisting of (1:2) Al$_2$O$_3$/epoxy, (1:2) Al$_2$O$_3$/epoxy+(3:10) Cu/epoxy and (2:1) 18-8 stainless steel/epoxy+(3:10) Al$_2$O$_3$ epoxy, presented thermal, frictional and surface wear characteristics equivalent to 316 stainless steel when run in distilled water against UHMWPE. The addition of Cu to the Al$_2$O$_3$/epoxy dramatically increased the thermal conductivity and reduced the UHMWPE wear scar width when run dry. The addition of 18-8 stainless steel to the Al$_2$O$_3$ epoxy reduced the wear scar width and coefficient of friction when run dry against UHMWPE. There was some visual evidence of UHMWPE transfer to the surface of the (1:2) Al$_2$O$_3$/epoxy+(3:10) Cu/epoxy when this material was run dry against the UHMWPE.

Figure 7:
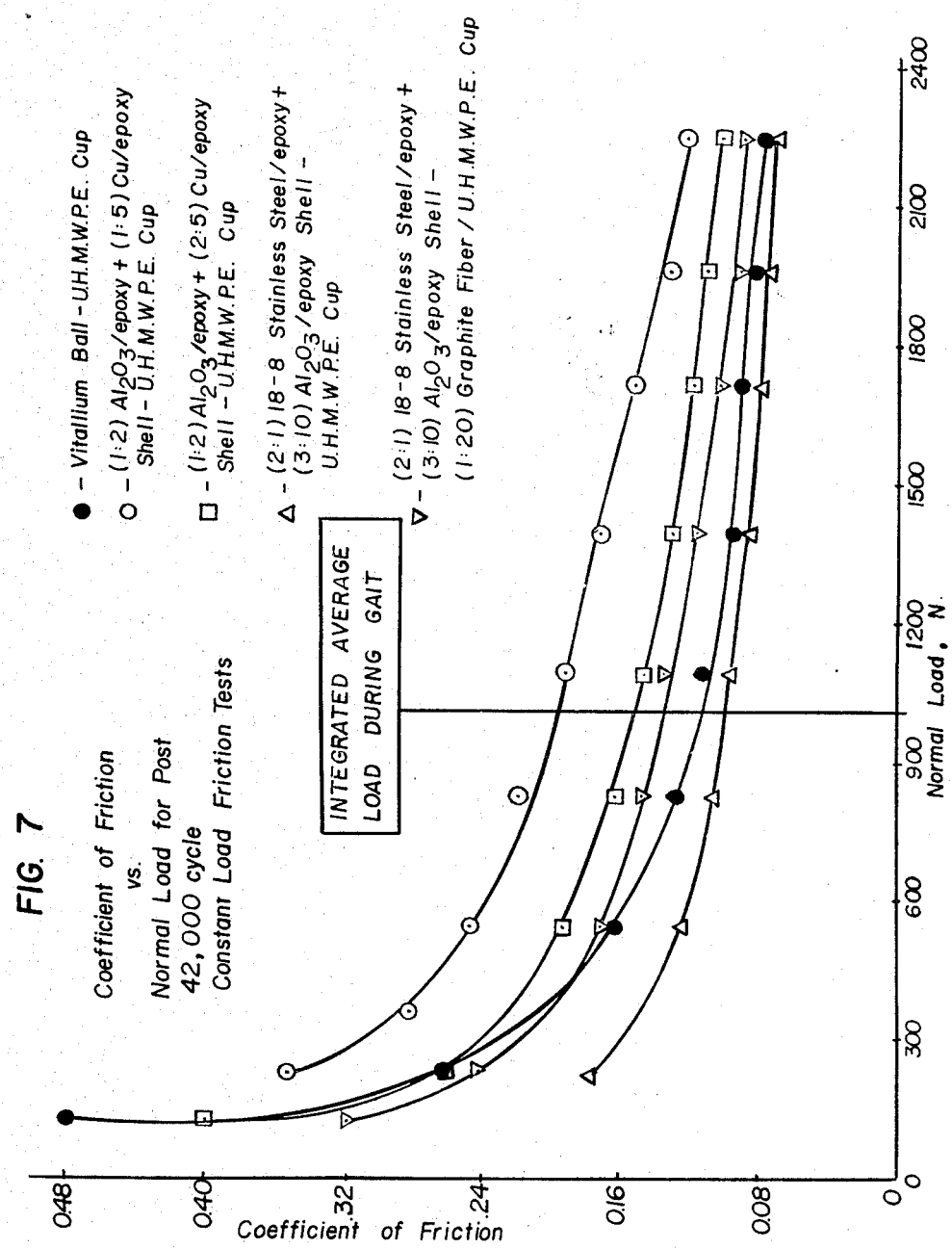
FIG. 7 is a graph showing the coefficient of friction related to load of the inventive coating and a vitallium ball for comparison.
Figure 8:
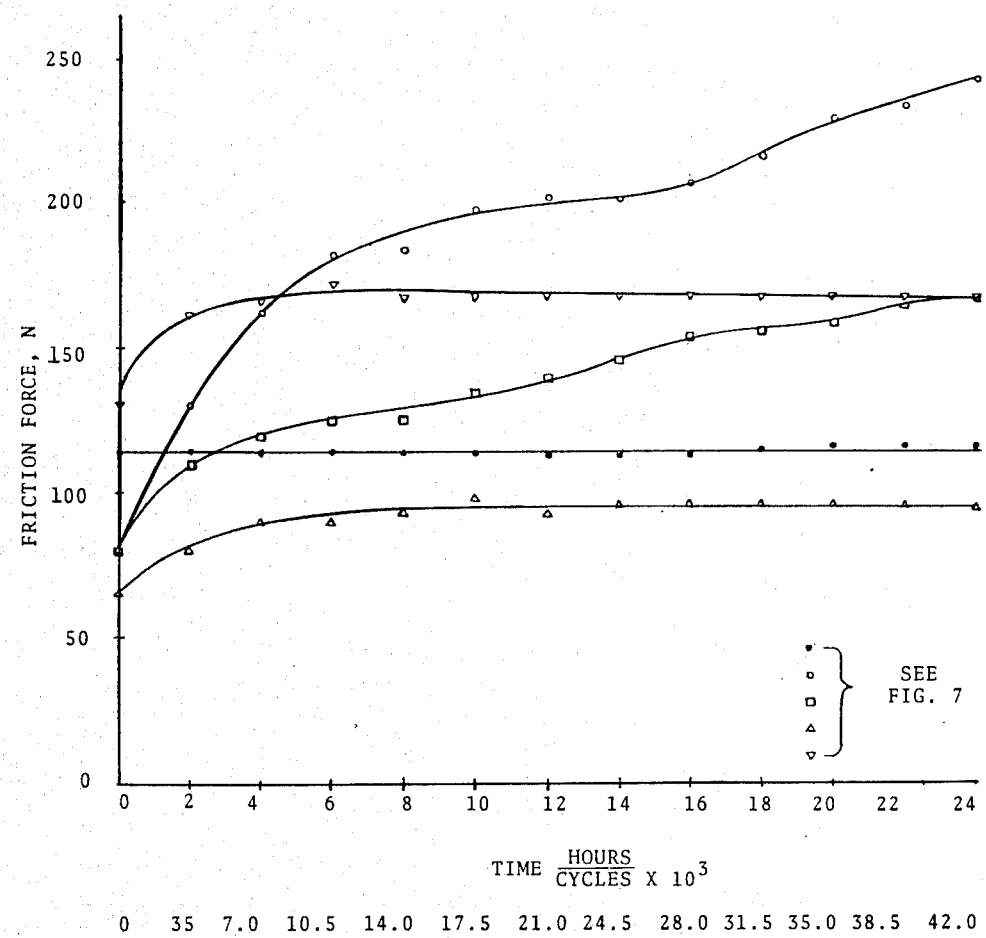
FIG. 8 is a graph relating frictional force to time of the inventive coating and a vitallium ball, for comparison.

According to a major object of the invention therefor a replacement hip joint according to FIG. 1 can be produced which more closely mimics a natural healthy hip joint in its characteristics. The invention according to FIG. 1 was tested for 42,000 cycles and 250,000 cycles of articulation and compared to prior art prosthetic hip joint designs. Some of the results of these tests are shown in FIGS. 7 and 8. These graphs illustrate the effectiveness of the design as compared to the prior art vitallium ball designs. These advantageous results were achieved even with the increased elasticity and other advantages of the inventive design.

The plastic shell 12 can be thin and comparable in thickness to the prior art metal shells used for the same purpose. The proportions for the various components of the acrylic matrix coating can vary from those specifically set forth above. The epoxy component can be from 2 to 30 parts by weight of the total coating with the Al$_2$O$_3$ component being from 1 to 5 parts by weight.

Where Cu or stainless steel granules are added these may be in a proportion of 0 to 7 parts by weight of the whole. The preferred range of particle sizes is 1 to 64 microns for Al$_2$O$_3$, 1 to 30 microns for Cu and 1 to 64 microns for the stainless steel. While a specific epoxy resin with hardener has been disclosed, other epoxy resins can be used as follows: polyfunctional epoxidized phenol novolac resin with a liquid anhydride hardener, aliphatic diacid glycidyl esters and 1,4-Bis[(2-3)-epoxypropoxy dimethylsilyl]benzene.

While specific embodiments of the invention have been shown and described in detail to illustrate the application of the principles of the invention, it will be understood that the invention may be embodied otherwise without departing from such principles.

What is claimed is:

1. A prosthetic joint for engaging a bone head in a body socket, the bone head having a trabecular structure and a modulus of elasticity, comprising:

a cup adapted to be secured in the body socket; and a shell having a matrix of cured epoxy resin adapted to be secured over the bone head and slidably engaged in said cup;

said shell having a composite coating in sliding engagement with said cup which is made of from 2 to 30 parts by weight epoxy, from 1 to 5 parts by weight Al$_2$O$_3$ and from 1 to 10 parts by weight metallic substance chosen from the group consisting of Cu and stainless steel;

said epoxy matrix including reinforcing glass fibers embedded therein and oriented with the trabecular structure of the bone head, said glass fibers being provided in an amount to cause said matrix to mimic the modulus of elasticity of the bone head.

2. A prosthetic joint according to claim 1, wherein the particle size of Al$_2$O$_3$ is from 1 to 64 microns, the particle size of Cu is from 1 to 30 microns and the particle size of stainless steel is from 1 to 64 microns.

3. A prosthetic joint according to claim 1 wherein said cup is made of ultra-high molecular weight polyethylene.

* * * * *